United States Patent
Miraki et al.

Patent Number: 5,827,202
Date of Patent: Oct. 27, 1998

[54] GUIDE WIRE DISPENSER APPARATUS AND METHOD

[75] Inventors: Manoucher Miraki; Robert Pecor, both of Aliso Viejo; Donald E. Bobo, Jr., Santa Ana; Ryszard Cieslak, Vista; Dennis Workman, Anaheim, all of Calif.

[73] Assignee: Baxter International Inc., Deerfield, Ill.

[21] Appl. No.: 822,890

[22] Filed: Mar. 24, 1997

Related U.S. Application Data

[63] Continuation-in-part of Ser. No. 662,748, Jun. 10, 1996.

[51] Int. Cl.$^6$ .......................................................... A61B 5/00
[52] U.S. Cl. ............................. 600/585; 600/433; 604/95; 604/280
[58] Field of Search ...................................... 600/585, 433, 600/434, 435; 604/95, 96, 280, 281, 282

[56] References Cited

U.S. PATENT DOCUMENTS

| | | |
|---|---|---|
| 3,416,531 | 12/1968 | Edwards . |
| 3,521,620 | 7/1970 | Cook . |
| 3,561,445 | 2/1971 | Katerndahl et al. . |
| 3,682,173 | 8/1972 | Center . |
| 3,774,605 | 11/1973 | Jewett . |
| 3,826,256 | 7/1974 | Smith . |
| 3,835,854 | 9/1974 | Jewett . |
| 3,847,140 | 11/1974 | Ayella . |
| 3,995,628 | 12/1976 | Gula et al. . |
| 4,003,369 | 1/1977 | Heilman et al. . |
| 4,020,829 | 5/1977 | Willson et al. . |
| 4,080,706 | 3/1978 | Heilman et al. . |
| 4,160,451 | 7/1979 | Chittenden . |
| 4,173,228 | 11/1979 | Van Steenwyk et al. . |
| 4,205,675 | 6/1980 | Vaillancourt . |
| 4,215,703 | 8/1980 | Willson . |
| 4,274,408 | 6/1981 | Nimrod . |
| 4,311,139 | 1/1982 | Smith . |
| 4,342,313 | 8/1982 | Chittenden . |
| 4,397,091 | 8/1983 | Gustavsson et al. . |
| 4,417,886 | 11/1983 | Frankhouser et al. . |
| 4,425,908 | 1/1984 | Simon . |
| 4,534,363 | 8/1985 | Gold . |
| 4,540,404 | 9/1985 | Wolvek . |
| 4,569,347 | 2/1986 | Frisbie . |
| 4,650,472 | 3/1987 | Bates . |
| 4,652,256 | 3/1987 | Vaillancourt . |
| 4,676,249 | 6/1987 | Arenas et al. . |
| 4,724,846 | 2/1988 | Evans, III . |
| 4,726,369 | 2/1988 | Mar . |
| 4,795,434 | 1/1989 | Kujawski . |
| 4,799,496 | 1/1989 | Hargreaves et al. . |
| 4,813,938 | 3/1989 | Raulerson . |
| 4,824,435 | 4/1989 | Giesy et al. . |
| 4,844,092 | 7/1989 | Rydell et al. . |
| 4,854,325 | 8/1989 | Stevens . |
| 4,858,810 | 8/1989 | Intlekofer et al. . |
| 4,860,757 | 8/1989 | Lynch et al. . |

(List continued on next page.)

FOREIGN PATENT DOCUMENTS

| | | |
|---|---|---|
| 534747A1 | 3/1993 | European Pat. Off. . |
| 0 587 984 | 5/1993 | European Pat. Off. . |
| 207 358 | 11/1968 | U.S.S.R. . |
| WO 97/18850 | 5/1997 | WIPO . |

*Primary Examiner*—Max Hindenburg
*Assistant Examiner*—Pamela A. Wingood
*Attorney, Agent, or Firm*—David J. Oldenkamp; Bruce M. Canter; Guy L. Cumberbatch

[57] ABSTRACT

A guide wire dispenser which is used to introduce a guide wire into the body using one hand. The dispenser utilizes a trigger grip configuration which is arranged in combination with a thumb access platform to provide accurate single-handed control of guide wire delivery to the body. A dual trigger configuration is also disclosed which provides the capability to dispense a guide wire from two different nozzles in a single device.

31 Claims, 4 Drawing Sheets

U.S. PATENT DOCUMENTS

| | | |
|---|---|---|
| 4,917,094 | 4/1990 | Lynch et al. . |
| 5,125,906 | 6/1992 | Fleck . |
| 5,186,179 | 2/1993 | MacEachern . |
| 5,273,042 | 12/1993 | Lynch et al. . |
| 5,325,746 | 7/1994 | Anderson . |
| 5,366,444 | 11/1994 | Martin . |
| 5,438,993 | 8/1995 | Lynch et al. . |
| 5,448,993 | 9/1995 | Lynch et al. . |
| 5,484,419 | 1/1996 | Fleck . |
| 5,499,632 | 3/1996 | Hill, III et al. . |

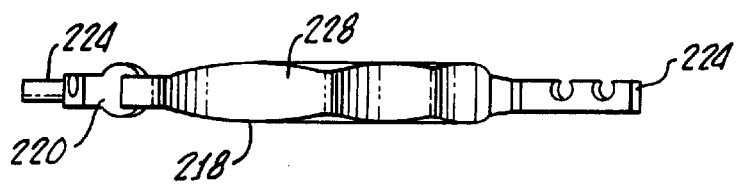
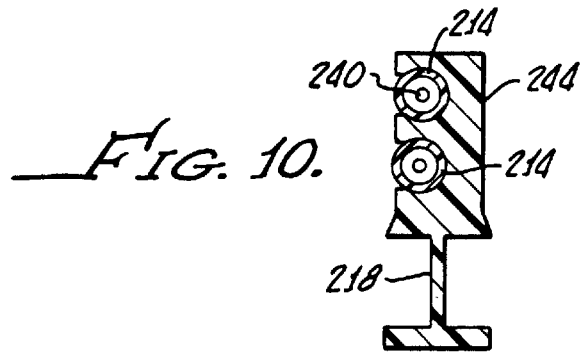
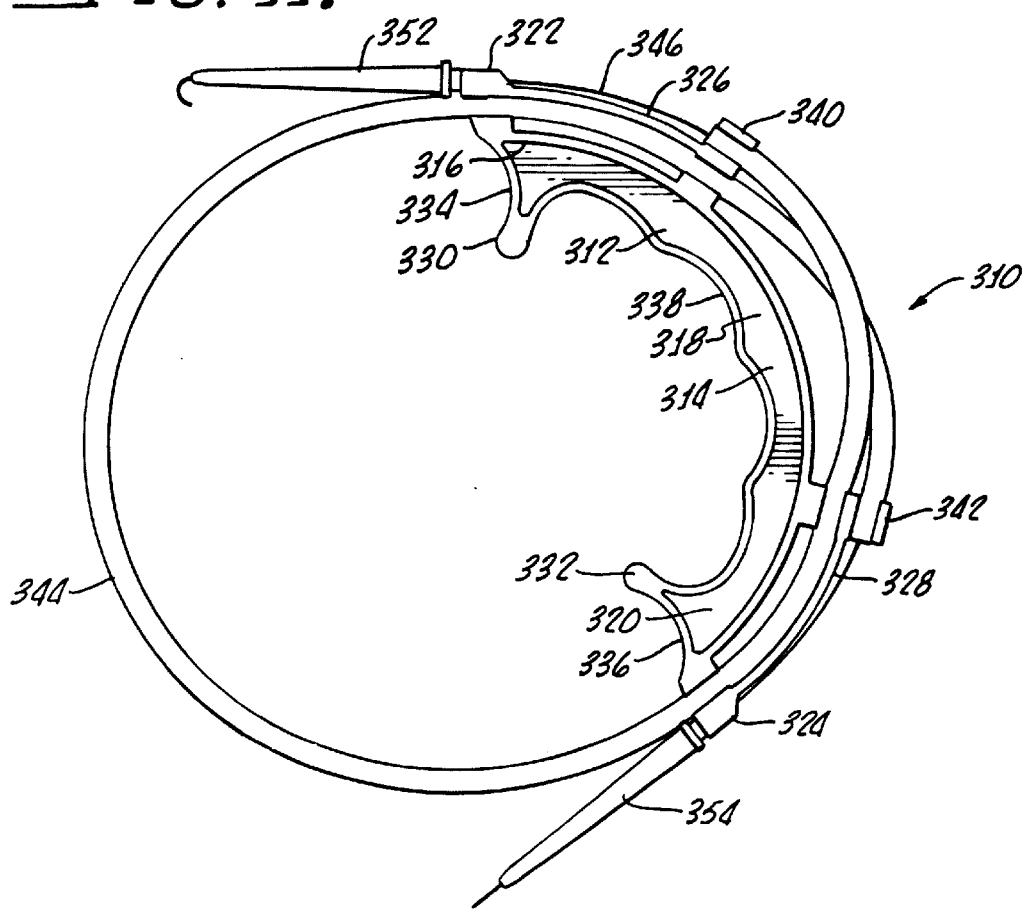

GUIDE WIRE DISPENSER APPARATUS AND METHOD

This is a continuation-in-part of copending application Ser. No. 08/662,748 which was filed on Jun. 6, 1996.

BACKGROUND OF THE INVENTION

Field of the Invention

In a broad aspect, the present invention is related to the field of medical guide wires. More particularly, the present invention is directed to the field of guide wire storage, dispensing, and manipulation apparatus and methods used to store, transport, and dispense guide wires in any medical procedure utilizing a guide wire to introduce a device into a body. For example, the present invention may be used in connection with the intravascular placement of medical devices, particularly the placement of central venous catheters, percutaneous introducers, intravascular monitoring catheters and in the performance of angioplastic cardiac catheterization.

Related Technology

As the need to access the interior of the human body has expanded in order to diagnose, monitor, and treat a variety of medical conditions, numerous techniques have been developed to provide the attending physician and medical personnel with the ability to accurately position medical devices within a patient's body and to access seemingly remote areas within a patient's vasculature. One of the more popular techniques utilizes a simple, yet effective, medical device known as a guide wire. Medical guide wires range from inches to feet in length and typically are formed of surgical grade stainless steel or similar material. Because they are formed with very small diameters measured in the thousandths of an inch they are highly flexible; yet, because of the inherent stiffness and resiliency of the materials from which they are formed, physicians and medical personnel are able to easily insert and direct guide wires through tortuous vascular pathways or into body cavities and other locations.

By pushing and rotating the proximal end of the guide wire outside of the patient the physician is able to direct the distal end of the guide wire to the desired target site. Typically, the distal end of the guide wire is provided with a relatively soft, atraumatic flexible tip which may be formed of radiopaque material to facilitate fluoroscopic visualization of the guide wire as it is advanced within a patient's body. Once in place, a wide variety of medical devices may be directed to the target site along the guide wire by simply sliding a lumen or channel formed in the device over the guide wire to advance the device to the distal tip. Following placement of the device, the guide wire can be removed if desired.

One widely practiced method for the intravascular placement of guide wires and, subsequently, medical devices, is known as the modified Seldinger approach. Utilizing this technique, physicians or medical personnel first verify vascular access utilizing a syringe with an appropriately sized hypodermic needle. To verify that the needle has accessed the appropriate vascular pathway, the syringe is utilized to pull a visible sample of blood through the hypodermic needle where it can be observed by the physician. Following confirmation of vascular access, the syringe is removed leaving the appropriately gauged hypodermic needle in position within the vascular pathway. The physician then inserts the distal end of the guide wire into the hypodermic needle hub and then advances the remaining length of the guide wire intravascularly to the target site.

As those skilled in the art will appreciate, in order to access remote regions deep within a patient's vasculature or other body location, a correspondingly sized guide wire must be used. Additionally, if relatively lengthy medical devices are to be advanced effectively along the guide wire a correspondingly sized portion of the guide wire must extend out of the patient's body to allow the physician to thread the device onto the proximal end of the guide wire without losing control of the guide wire placement within the patient's body. As a result, it is not uncommon for guide wires to extend many feet in length. Thus, maintaining control of the lengthy guide wire during its placement and use can be complicated and awkward.

Early solutions to such problems relied upon the simple expedient of providing an additional pair of hands in the form of a medical assistant who would be charged with controlling the external portion of the guide wire as the guiding physician or medical personnel would advance and position the distal end of the guide wire within the patient. Though acceptable, this technique proved to be quite costly and added to the crowding and potential for confusion within the operating room and the intensive care environment. More recent approaches directed toward solving the problem of guide wire dispensing and control have utilized hand held devices to manipulate and store the guide wire.

U.S. Pat. No. 5,125,906, issued 30 Jun. 1992, to Phillip B. Fleck, is believed to disclose a hand-held device for feeding or dispensing a guide wire. The device according to the '906 patent appears to include a handle-like apparatus having a length of tubing forming a housing and opening for dispensing a guide wire. The handle defines a tubular barrel member opening to an axial bore from which the guide wire dispenses, and a tubular rear end member opening to an end of the tubing in which the guide wire is stored. Intermediate of the barrel and rear end portions is an open straight section at which manual access to the guide wire can be achieved by use of the thumb and forefinger of a physician. The distal end portion of the barrel member includes a rather small bore in which a J-end portion of the guide wire is straightened for insertion into a syringe or needle for feeding the guide wire into an artery of a patient.

Another conventional guide wire advancer is known in accord with U.S. Pat. No. 5,273,042, issued 28 Dec., 1993, to Arthus S. Lynch, et al. The '042 patent is believed to teach a guide wire storage and advance device in which a loop of tubing is terminated in a straight tangential portion leading to an open end of the tubing. At the open end of the tubing, a straightener member is receivable into an end portion of the tubing to be secured thereto. Adjacent to the straight tangential portion of the tubing, an opening is formed at which manual access to the guide wire may be had by use of the thumb.

U.S. Pat. No. 5,366,444, issued 22 Nov., 1994, to Geoffrey S. Martin is believed to disclose yet another conventional device for feeding a guide wire. The device of the '444 patent also appears to include a length of tubular material formed into a loop. At one end of the loop of tubular material, a discharge head is joined to the tubing and includes a guide opening and an outlet tip with a discharge opening. Formed between the guide opening and the discharge tip is a straight platform over which the guide wire slides and at which manual access to the guide wire may be made by the use of a thumb to advance and retract the guide wire.

Finally, EP publication 0 587 984 A1, dated 5 May, 1993, is believed to disclose a guide wire dispenser device in which a coiled tubing is attached at one end to a handle portion having a guide bore for receiving the end of the coiled tubing, and a spaced away tip portion having a bore through which the guide wire passes. Between the guide bore and the tip is defined an essentially straight platform at which manual access to the guide wire may be had. The tip bore is apparently offset somewhat relative to the guide bore, and the handle portion has a pair of oppositely curved lower portions leading to a clip-like feature capturing the opposite end of the tubing, all apparently to enhance the ergonomics of the device.

A persistent problem with conventional guide wire storage and dispensing apparatus is that the guide wires are inherently springy and difficult to control with one hand. The storage and dispensing apparatus conventionally employs a length of coiled tubing to store the guide wire prior to its being dispensed into a patient during introduction or intravascular placement of a medical device. Further, the coefficient of friction between the guide wire and the tubing in which it is stored is not very high which complicates storage and dispensing of the wire. Low friction is to be expected, and is desirable in some respects, because the guide wire is dispensed from the device using only that purchase on the guide wire which can be gained by the application of manual pressure and friction with one or more fingers, usually with the thumb alone. On the other hand, this relatively low coefficient of friction allows the guide wire to creep out of the conventional dispensers due to its own springiness, and due to jostling which occurs in shipping and handling. In some cases, physicians have the experience of having the guide wire advance out of the dispenser, or self-eject, under the influence of its own springiness. In the event where the guide wire self-ejects and contacts non-sterile environmental surfaces the wire cannot thereafter be introduced into a patient because of the risk of infection and must be discarded.

SUMMARY OF THE INVENTION

In view of the deficiencies of the conventional technology outlined above, it is a primary object for this invention to avoid one or more of the deficiencies of the prior art with a simple and inexpensive apparatus.

Yet another object for the present invention is to provide a storage, transport, and dispensing apparatus for a guide wire which prevents the guide wire from self-ejecting.

Still another object for this invention is to provide such a storage, transport, and dispensing apparatus for a guide wire in which the guide wire is required to form an arch or arcuate section having a slight reverse bend or arcuate bend at each end, and intermediate of which the guide wire is exposed for manual advancing and retracting access.

According to one embodiment, the present invention provides a storage and dispensing apparatus for a guide wire, the apparatus including a wrap of elongate tubing having a bore for receiving an elongate guide wire, a first end, a tangential portion extending from said wrap and terminating at an open second end, adjacent to said tangential portion the elongate tubing defining a pair of spaced apart apertures opening from the bore radially outwardly on the tubing, and an outer curved surface portion extending along the length dimension of the tubing intermediate of the pair of openings across which a curved portion of the guide wire may extend and be accessible for manual manipulation to advance and retract the guide wire through the open second end; and means for providing manual purchase on the wrap of tubing. The means for providing manual purchase may be configured as a handle, which also may include features for constraining the tubing in a spiral shape.

A better understanding of the present invention will be obtained from reading the following description of two preferred exemplary embodiments of the present invention when taken in conjunction with the appended drawing Figures, in which the same features (or features which are analogous in structure or function) are indicated with the same reference numeral throughout the several views. It will be understood that the appended drawing Figures and description here following relate only to one or more exemplary preferred embodiments of the invention, and as such, are not exhaustive and do not imply a limitation on the invention. No such limitation on the invention is implied, and none is to be inferred.

BRIEF DESCRIPTION OF THE DRAWING FIGURES

FIG. 1 provides a fragmentary view showing a storage and dispensing apparatus according to the present invention in use by a physician to dispense a guide wire therefrom into a patient;

FIG. 9 is a top view of the handle body shown in FIG. 8;

FIG. 10 is a sectional view of FIG. 7 taken in the 10—10 plane; and

FIG. 11 is a third guide wire dispenser in accordance with the present invention.

DETAILED DESCRIPTION OF TWO EXEMPLARY PREFERRED EMBODIMENTS OF THE INVENTION

Figure 1:
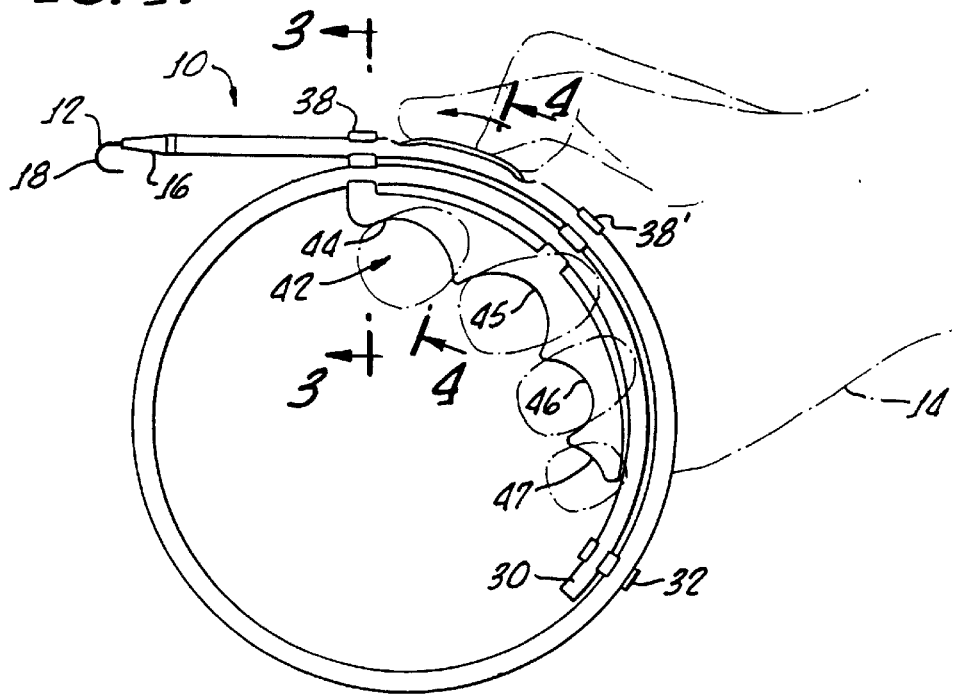
Figure 2:
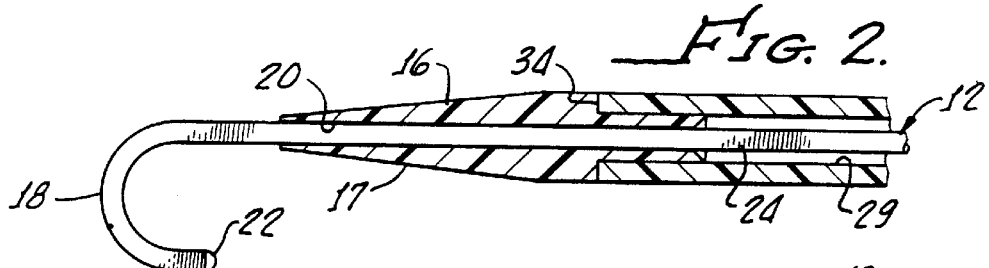
FIG. 2 is an enlarged fragmentary cross sectional view of a portion of the apparatus shown in FIG. 1.

Viewing FIG. 1, a storage and dispensing apparatus 10 for a guide wire 12 is seen in use by a physician 14 to dispense the guide wire via a hypodermic needle (not shown) into the vasculature of a patient (also not shown) preparatory to the introduction of a medical device. Those ordinarily skilled in the pertinent arts will understand that the hypodermic needle is inserted into a selected artery of the patient, and the guide wire 12 is introduced into the external portion of the needle via a tapered introducer tip 16 of the apparatus 10. This introducer tip defines a conically tapering outer surface 17. Conventionally, the guide wire 12 includes a J-shaped flexible resilient end portion 18. The introducer tip 16 defines a bore portion 20 at the distal termination of the surface 17 (best seen in FIG. 2) closely receiving the resilient end portion 18 of the guide wire 12.

Consequently, in use of the apparatus 10, the physician 14 may withdraw the J-shaped end portion 18 into the bores 20 and 29 (as will be explained), thus straightening this end portion preparatory to introducing the tapered introducer into the exterior portion of the hypodermic needle. As the guide wire 12 is advanced from the tip 16 and into the hypodermic needle (as also will be explained), the portion 18 is maintained relatively straight. Once into an artery or vein, the J-shaped tip facilitates steering the guide wire to a treatment site. It will be noted in FIG. 2 that the portion 18 of guide wire 12 terminates at a radiopaque marker tip 22 which is used to visualize the position of the end of the guide wire 12 within a patient. Those ordinarily skilled in the pertinent arts will also recognize that behind the resilient portion 18 the guide wire 12 includes a rather stiff, elongate and pushable, but springy and resilient, shaft portion 24. This shaft portion 24 is received into a coiled tubular part 26 of the apparatus 10. More properly, this tubular part 26 can be seen to be spiral wrapped on itself. The introducer tip 16 extends from a tangential portion of the coiled or spiral wrapped part 26.

In order to form the coiled tubular part 26, a length of tubing 28 is spiraled on itself as shown in FIG. 1, and adjacent to an end 30 thereof remote from the tip 16 is secured in a clip member 32. Thus, the clip member 32 secures to the tubing 28 as shown in FIG. 1 so that a spiral of this tubing is formed. In order to distinguish the outer wrap of this spiral from an inner wrap or wraps, the outer wrap is referenced with the numeral 28', and each successive wrap inwardly has an additional prime added. Thus, in the illustrated embodiment which has only a single inner wrap of tubing 28, the inner wrap is referenced with the numeral 28". Those ordinarily skilled in the pertinent arts will recognize that the apparatus 10 may include more than one spiral wrap of tubing, depending upon the length of the guide wire contained therein. The tubing 28 defines a bore or longitudinal inner passage 29.

Adjacent to an end 34 at which a portion of the tip member 16 is received into the tubing 28 (viewing FIG. 2), the inner wrap 28" and outer wrap 28' of tubing 28 are secured at two spaced apart locations into a combined handle and clip member 36 (hereinafter referred to simply as a handle member). As will be discussed, this handle member 36 provides for secure manual purchase on the apparatus 10, even in an operating room environment possibly including blood and other liquids which could make the apparatus 10 slippery and difficult to grasp and control precisely. Viewing FIGS. 1, 3, and 5, it can be seen that the handle member 36 includes a pair of spaced apart clip portions 38 and 38', each of which defines a respective radially spaced pair of recesses 40 and 40' for respectively receiving each wrap 28', and 28" of the tubing 28.

Thus, the clip portions 38 and 38' each define a pair of recesses 40 and 40'. The wraps 28', 28" of the tubing 28 are respectively snapped into the recesses 40 and 40' and are there retained by their own resilience in combination with the resilience of the clip portions 38 and 38'. It will be understood that the wraps 28', 28" of tubing 28 may also be otherwise or additionally secured into the recesses 40, 40' such as by the use of an adhesive, although this may not be required.

Handle portion 36 also includes an arcuate digit-engagement section 42 disposed within the spiral of tubing 28 and defining a plurality of tandem digit-engaging recess portions 44, 45, 46, and 47, each disposed one behind the other, respectively, for engagement by the index finger to the little finger of the user. The one clip portion 38 extends radially outwardly from a position generally in alignment with the index-finger recess 44, while the other clip portion 38' extends radially outwardly from a position of general alignment with the middle-finger recess 45. The digit-engaging recess portions 44–47 are joined to one another, and the forward portion 44 is disposed slightly closer to the tubing wraps 28' and 28" in order to improve the ergonomics of the apparatus 10.

Figure 3:
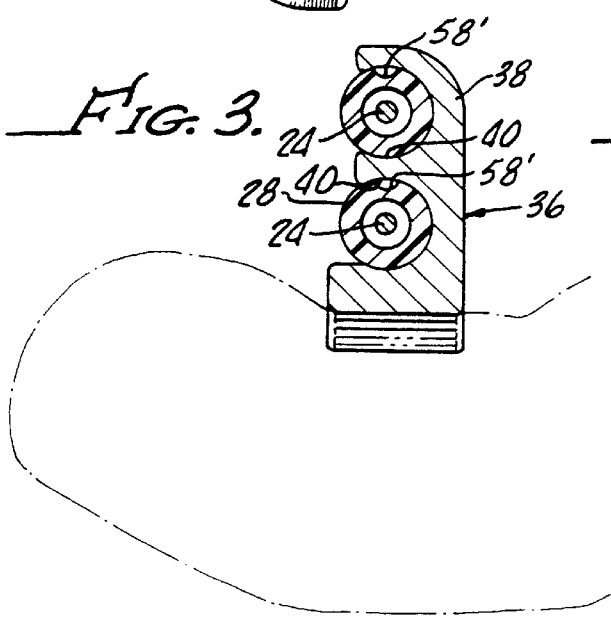
FIGS. 3 and 4 are respective enlarged fragmentary cross sectional views taken at the indicated planes of FIG. 1, and looking in the direction of the arrows.
Figure 5:
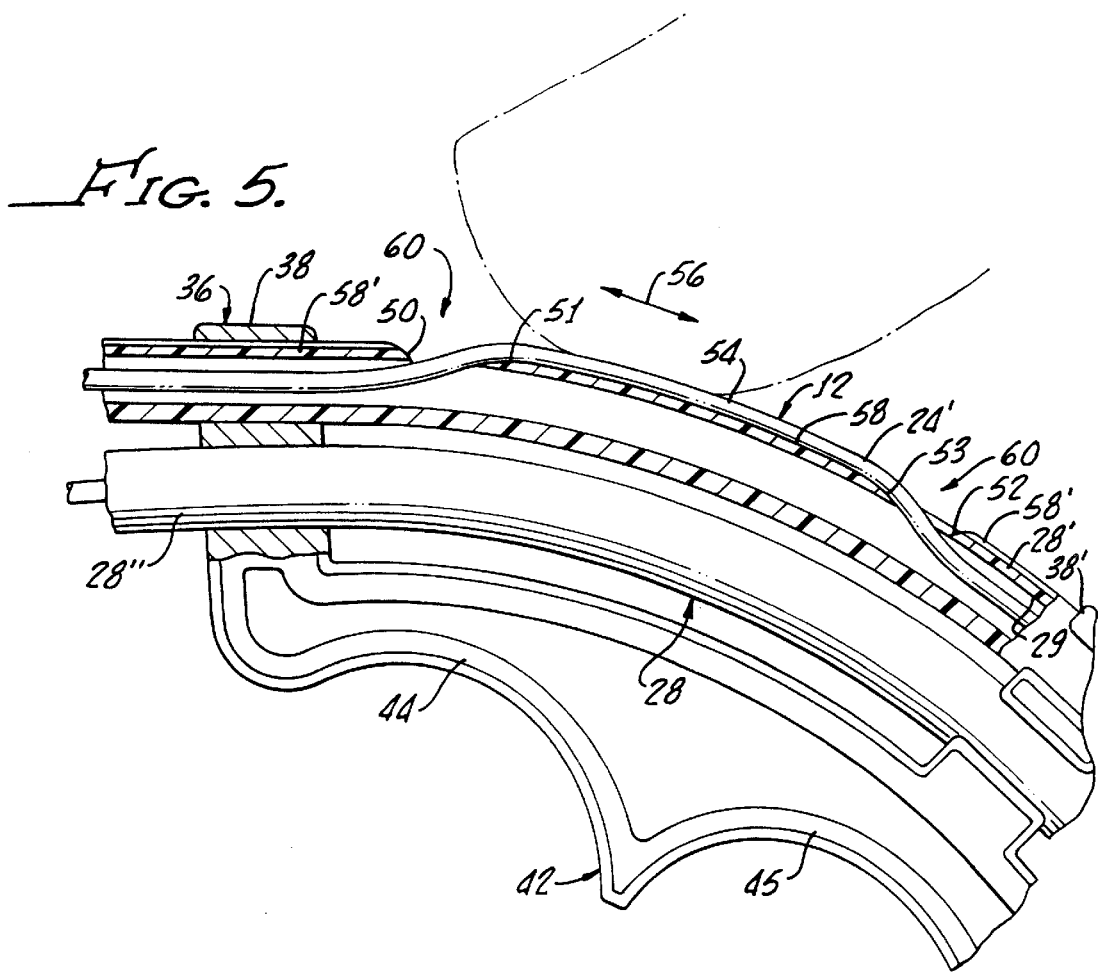
FIG. 5 is an enlarged fragmentary cross sectional view of a portion of the device shown in FIG. 1.

Each digit-engaging portion 44, 45, 46, and 47 defines a respective recess for receiving a finger of the physician's hand, as shown in FIGS. 1, 3, and 5. The fingers of the hand may be engaged by simply grasping the handle portion 36 with no need to insert fingers into rings or on opposite sides of a portion of tubing, as was the case with some of the conventional devices discussed above. This facility of the apparatus 10 improves the speed and utility of its use in an operating room environment. The tubing wraps 28' and 28" rearwardly of the digit-engaging portions 44–47 also cooperate with the handle portion 36 to provide an ergonomically appropriate and useful disposition of the apparatus 10 relative to a physician's hand and thumb for manipulating a guide wire.

Rearwardly of the clip portion 38 and forwardly of clip portion 38', the tubing 28 of the outer wrap 28' defines an outwardly disposed aperture 50 opening from the bore 29 radially outwardly on the tubing 28. Spaced rearwardly from the aperture 50 and forwardly of clip portion 38', the tubing 28 at outer wrap 28' defines another aperture 52 also opening radially from the bore 29 outwardly on the tubing 28. It will be noted that the apertures 50 and 52 are somewhat angular and are disposed angularly toward one another to define respective sloping surfaces 51 and 53. Intermediate of the openings 50 and 52, the tubing 28 defines an outer surface portion 54 across which the guide wire 12 extends. At this position guide wire 12 is available for manual access as depicted in FIGS. 1 and 5 to both advance and retract the guide wire, as illustrated by arrow 56 in FIG. 5. Guide wire shaft 24 extends out of the openings 50, 52, and runs lengthwise of tubing 28 along the curved surface portion 54, there to define a portion 24' accessible for manual contact and movement. Consequently, between the openings 50 and 52, as shown in FIG. 5, the tubing 28 at outer wrap 28' defines a bore portion 29' of bore 29 which is empty because the guide wire 12 is disposed outside of the tubing between the openings 50 and 52.

Figure 4:
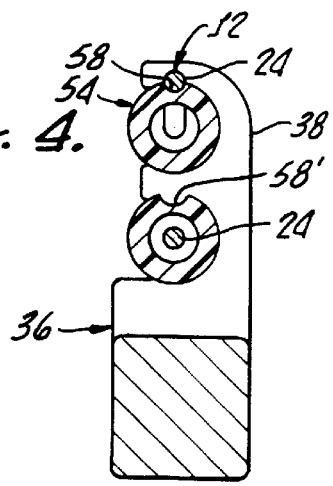

In order to provide lateral constraint of the guide wire 12 (i,e,. of shaft portion 24') between the openings 50 and 52, a groove 58 is formed on the curved outer surface 54 of the tubing 28 and extends between the openings 50 and 52. Groove 58 is disposed in the plane of the spiral of tubing 28, as shown in FIG. 4. The groove 58 may be formed by any convenient method. However, a particularly preferred way of forming groove 58 is to extrude the tubing 28 with a longitudinal groove 58' (best shown in FIGS. 3, 4, and 5) along its entire length, and to spiral wrap the tubing 28 to form the part 26 with the pre-formed groove 58' disposed radially outwardly, as shown in FIGS. 3, 4, and 5. When the openings 50 and 52 are formed in the tubing 28, a portion of the preformed groove 58' extends between these openings and defines groove 58. Because of the presence of groove 58, a portion 24' of the guide wire shaft 24 lays in this groove and is conveniently accessible by the physician's thumb to manually advance and retract the guide wire 12 with a single hand, as shown in FIGS. 1 and 5.

Also, because the guide wire shaft 24 forms a mild S-shaped bend 60 at each of the openings 50 and 52, the frictional engagement of guide wire 12 with tubing 28 is improved, and self-ejection of the guide wire from apparatus 10 is inhibited. That is, the engagement of guide wire 12 with tubing 28 is not so tenacious that the physician cannot easily advance and retract the guide wire manually, it is just sufficient that the guide wire 12 will not self-eject from storage and dispensing apparatus 10.

Figure 6:
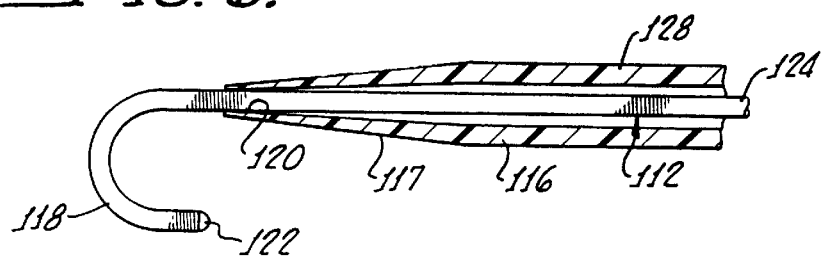
FIG. 6 is an enlarged fragmentary cross sectional view similar to that of FIG. 2, but showing an alternative embodiment of the invention.

Considering now FIG. 6, an alternative embodiment of the present guide wire storage and dispensing apparatus is depicted in fragmentary cross sectional view. In order to obtain reference numerals for use in describing this alternative embodiment of the invention, features which are the same as or equivalent in structure or function to those of the earlier embodiment are referenced with the same numeral used above, and increased by one-hundred (100). This view of FIG. 6 will be seen to be similar to that of FIG. 2, except that the distal end portion of the tubing 128 is integrally formed to define an introducer tip 116. The introducer tip 116 defines a conically tapering outer surface 117 terminating at a bore 120 slidably receiving the guide wire 112. This integral introducer tip offers the advantage of allowing insertion of the guide wire directly from the apparatus 10. In the event that a physician wants to manually manipulate the guide wire with two or more fingers, the apparatus 10 may simply be backed off slightly from the hypodermic needle, and access to the guide wire 112 is then possible intermediate of the device and the patient.

While the present invention has been depicted, described, and is defined by reference to two particularly preferred embodiments of the invention, such reference does not imply a limitation on the invention, and no such limitation is to be inferred. The invention is capable of considerable modification, alteration, and equivalents in form and function, as will occur to those ordinarily skilled in the pertinent arts. For example, while the present invention has been depicted and is described with reference to embodiments in which the elongate tubing is spiral wrapped on itself, the invention is not so limited. For example, the elongate tubing could be helically wrapped on itself, in which case the helical wraps of tubing would lay adjacent to one another in the user's hand. This arrangement would still allow the user to have access to the guide wire adjacent to an end of the coiled tubing.

Figure 7:
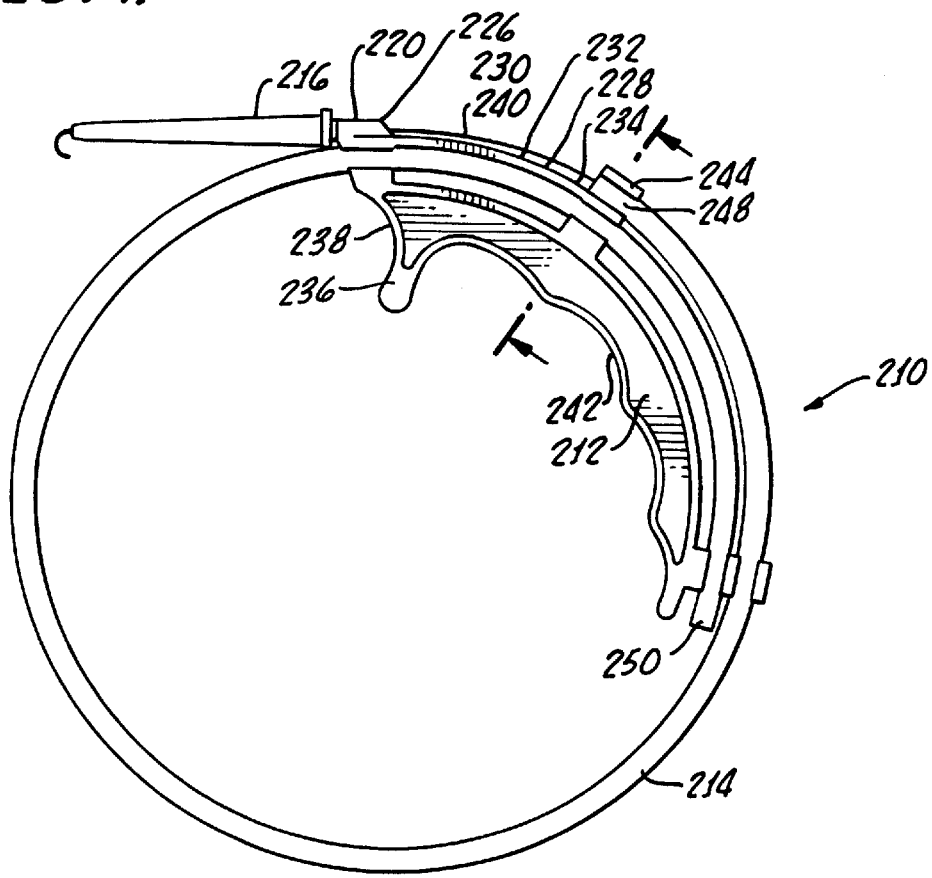
FIG. 7 is a side view of a second guide wire dispenser in accordance with the present invention showing the handle body, nozzle sheath and guide wire storage housing connected together.
Figure 8:
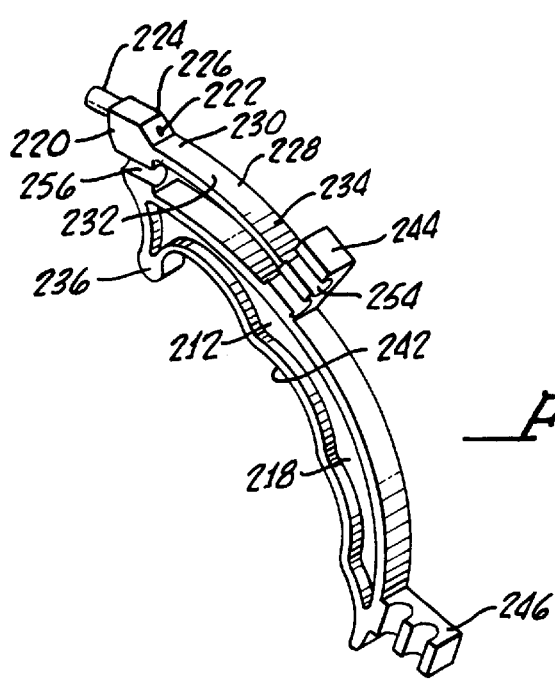
FIG. 8 is a perspective view of the handle body of FIG. 8 with the guide wire storage housing and nozzle sheath being removed.

A second guide wire dispenser in accordance with the present invention is shown generally at 210 in FIG. 7. The dispenser 210 includes a trigger grip handle 212, a guide wire storage housing 214, and a removal nozzle sheath 216. As best shown in FIG. 8, the trigger grip handle 212 includes a handle body 218 which has a wire dispensing nozzle 220. A wire dispensing conduit 222 passes through nozzle 220. The wire dispensing nozzle 220 includes a proximally located head portion 224 and a distally located rear portion 226. The handle body 218 further includes a thumb platform 228. The thumb platform 228 includes a forward section 230, middle section 232, and rearward section 234.

The handle body 218 also includes a trigger finger grip 236. The surface 238 of the trigger finger grip 236 is shaped to receive the index finger of the user in the same manner as the index finger recess 44 shown in FIG. 1. As an important feature of this particular embodiment, the trigger grip 236 is located below the forward section 230 of the thumb platform 228. The shape of the trigger grip 236 and location relative to the thumb platform 230 provides a particularly effective positioning of the user's hand so that the thumb may accurately and controllably contact the guide wire 240. By comparison, the location of the trigger grip 236 with respect to the thumb platform 230 provides the same feel to the user's hand as gripping a handgun wherein the thumb is used to manually operate the gun hammer. Although the location of the trigger grip 236 relative to the thumb platform may be moved forward or rearward slightly, it is preferred that the trigger grip be located substantially as shown in FIG. 7.

The handle body 218 further includes a handle grip surface 242 which is shaped to receive the remaining three fingers of the operator.

The nozzle sheath 216 may be removed to leave the exposed head portion 224 of the nozzle 224 as shown in FIG. 7. In addition, the guide wire storage housing 214 may also be removed. Preferably, the guide wire storage housing 214 is made from plastic tubing which can be press-fit into mounting tabs 244 and 246. The guide wire storage housing has a proximal end 248 and a distal end 250. The proximal end is press-fit into a mating groove 254 in mounting tab 244. An additional groove 256 is provided below the nozzle 220 for providing an additional anchoring location for the storage housing 214.

The thumb platform 228 may be flat or curved. It is preferred that the platform 228 be curved to match the radius of curvature of the handle body 218 as best shown in FIG. 7.

A third guide wire dispenser in accordance with the present invention is shown generally at 310 in FIG. 11. The dispenser 310 is similar to dispenser 210, except that an additional trigger grip is provided on the opposite end of the handle body to allow dispensing of a guide wire in two different directions. The dispenser 310 includes a trigger grip handle 312 which includes a handle body 314 which has a first end 316, middle portion 318, and second end 320. The handle body 314 further includes a first wire dispensing nozzle 322 and a second wire dispensing nozzle 324. A thumb platform 326 is located adjacent to nozzle 322 with a second thumb platform 328 being located adjacent to second nozzle 324. A first trigger grip is located at 330 with the second trigger grip being located at 332. The two trigger grips 330 and 332 are positioned to provide trigger finger gripping surfaces 334 and 336, respectively, which are positioned relative to their respective thumb platforms in the same manner as the single trigger grip dispensing system shown in FIG. 7. The central handle grip surface 338 is shaped to receive the remaining three fingers of the user's hand when either trigger grip 330 or 332 is being used. Two mounting tabs 340 and 342 are provided to mount the guide wire housing 344 to provide placement of the guide wire 346 over the two thumb platforms 326 and 328.

The guide wire dispenser 310 is operated in the same manner as the other exemplary dispensers 10 and 210, except for the added feature of having two trigger grips and thumb platforms in a single device. Removable sheaths 352 and 354 are provided to cover the nozzles 322 and 324, respectively.

The above depicted and described preferred embodiments of the invention are exemplary only, and are not exhaustive of the scope of the invention. Consequently, the invention is intended to be limited only by the spirit and scope of the appended claims, giving full cognizance to equivalents in all respects.

We claim:

1. A guide wire dispenser adapted for introducing a guide wire into the body using one hand, said hand having an index finger, a thumb for friction contact with said guide wire to provide thumb-controlled dispensing of said guide wire and three remaining fingers for gripping said guide wire dispenser, said guide wire dispenser comprising:

a) a trigger grip handle comprising:

a handle body comprising a wire dispensing nozzle having a wire dispensing conduit located therethrough, said wire dispensing nozzle comprising a proximally located head portion from which said guide wire is dispensed and a distally located rear portion into which said guide wire is received, a thumb platform connected integrally to said rear portion of said dispensing nozzle and extending distally therefrom, said thumb platform comprising a forward section, middle section and rearward section;

a trigger finger grip surface which is located on said trigger grip handle below said forward section of said thumb platform, said trigger finger grip surface being shaped to receive the index finger of said single hand used to introduce said guide wire into said body;

a handle grip surface which is located distally of said trigger finger grip surface, said handle grip surface being shaped to receive said remaining three fingers; and b) a guide wire storage housing comprising a proximal end located at the rearward section of said thumb platform, a coiled central portion for containing a guide wire, and a distal end, said proximal end being located so as to provide introduction of a guide wire onto said thumb platform, and wherein a portion of said coiled central portion is attached to said trigger grip handle between the handle body and the trigger finger grip and handle grip surfaces so that in use, the thumb of the user is positioned outside of said coiled central portion over the thumb platform and the fingers are positioned in the trigger finger grip and handle grip surfaces inside of said coiled central portion.

2. A guide wire dispenser according to claim 1 wherein said thumb platform is arcuate in shape.

3. A guide wire dispenser system according to claim 1 which further comprises a guide wire located within said guide wire storage housing.

4. A guide wire dispenser system according to claim 1 wherein a removable sheath is attached to said wire dispensing nozzle said sheath having a base portion adapted for removable mating attachment to the head portion of said nozzle and a tip portion having an opening through which said guide wire is dispensed.

5. A guide wire dispenser system according to claim 1 wherein said handle body comprises at least one mounting tab for holding said guide wire storage housing in fixed relation to said handle body.

6. A guide wire dispenser system according to claim 5 wherein said handle body comprises two mounting tabs for holding said guide wire storage housing in fixed relation to said handle body.

7. A guide wire dispenser adapted for introducing a guide wire into the body using one hand, said hand having an index finger, a thumb for friction contact with said guide wire to provide thumb-controlled dispensing of said guide wire and three remaining fingers for gripping said guide wire dispenser, said guide wire dispenser comprising:

a) a trigger grip handle comprising:
a handle body comprising a first end, a second end and a central portion, said handle body further comprising a first wire dispensing nozzle located at said first end of said handle body and having a first wire dispensing conduit located therethrough, said first wire dispensing nozzle comprising a head portion from which said guide wire is dispensed and a rear portion into which said guide wire is received, a first thumb platform connected integrally to said rear portion of said first wire dispensing nozzle and extending therefrom towards the central portion of said handle body, said first thumb platform comprising a forward section, middle section and rearward section, said handle body further comprising a second wire dispensing nozzle located at said second end of said handle body and having a second wire dispensing conduit located therethrough, said second wire dispensing nozzle comprising a head portion from which said guide wire is dispensed and a rear portion into which said guide wire is received, a second thumb platform connected integrally to said rear portion of said second wire dispensing nozzle and extending therefrom inward towards the central portion of said handle body, said second thumb platform comprising a forward section, middle section and rearward section;

a first trigger finger grip surface which is located on said trigger grip handle below said forward section of said first thumb platform, said first trigger finger grip surface being shaped to receive the index finger of said single hand used to introduce said guide wire into said body;

a second trigger finger grip surface which is located on said trigger grip handle below said forward section of said second thumb platform, said second trigger finger grip surface being shaped to receive the index finger of said single hand used to introduce said guide wire into said body;

a central handle grip surface which is located between said first and second trigger finger grip surfaces, said handle central handle grip surface being shaped to receive said remaining three fingers; and b) a guide wire storage housing comprising a first end located at the rearward end of said first thumb platform, said first end being located so as to provide introduction of a guide wire onto said first thumb platform, a central portion for containing said guide wire, and a second end located at the rearward end of said second thumb platform, said second end being located so as to provide introduction of said guide wire onto said second thumb platform.

8. A guide wire dispenser according to claim 7 wherein said first and second thumb platforms are arcuate in shape.

9. A guide wire dispenser system according to claim 7 which further comprises a guide wire located within said guide wire storage housing.

10. A guide wire dispenser system according to claim 7 wherein a removable sheath is attached to at least one of said first or second wire dispensing nozzles, said sheath having a base portion adapted for removable mating attachment to the head portion of said nozzles and a tip portion having an opening through which said guide wire is dispensed.

11. A guide wire dispenser system according to claim 7 wherein said handle body comprises a first mounting tab for holding the first end of said guide wire storage housing in fixed relation to said first thumb platform and a second mounting tab for holding the second end of said guide wire storage housing in fixed relation to said second thumb platform.

12. A storage and dispensing apparatus for a guide wire, the apparatus comprising:

a length of elongate tubing having a bore for receiving an elongate guide wire, a first end, and an open second end;

a handle including two clips for receiving and retaining the tubing in a spiral wrap, the handle having a digit-engagement section disposed within the spiral wrap defining a plurality of digit-engaging recesses formed in series along the inner curve of the spiral for receiving fingers of a user;

a curved outer platform rigidly attached to the handle concentrically located outside the curve of the spiral wrap and radially aligned with a portion of the digit-engagement section, the open second end of the elongate tubing being disposed to deliver the guide wire across the curved outer platform so as to be accessible for manual contact and sliding movement by the thumb of a user; and a wire dispensing nozzle secured to one end of the curved outer platform for closely receiving and tangentially dispensing the guide wire from the apparatus.

13. The apparatus of claim 12 wherein one of the digit-engaging recesses comprises a trigger finger recess radially aligned with the wire dispensing nozzle and shaped to receive an index finger of a user, and wherein the other digit-engaging recesses extend in series adjacent said trigger finger recess and are shaped to receive the remaining three fingers.

14. The apparatus of claim 13 wherein trigger finger recess opens in a direction generally tangential to the spiral wrap and the other digit-engaging recesses open radially inward.

15. The apparatus of claim 12 wherein the handle, curved outer platform and dispensing nozzle are molded as a single part.

16. The apparatus of claim 12 wherein the handle is formed in an arc having a curved outer wall from which the clips extend radially outward, the elongate tubing being held in close proximity and along the curve of the outer wall by the clips.

17. The apparatus of claim 16 wherein the curved outer platform is spaced from the curved outer wall and bridges the two clips.

18. The apparatus of claim 17 wherein the dispensing nozzle is formed as an outward extension of a forward one of the two clips, the second clip being spaced circumferentially therefrom in a rearward direction.

19. The apparatus of claim 18 further including a third clip for receiving and retaining the tubing in the spiral wrap spaced circumferentially rearward from the second clip.

20. The apparatus of claim 19 wherein the third clip has two recesses to receive adjacent loops of the spiral wrap of tubing.

21. The apparatus of claim 12 further including a tapered introducer tip removably received in the dispensing nozzle and extending tangentially with respect to the spiral wrap.

22. A guide wire dispensing apparatus, comprising:

a length of flexible elongate tubing having a bore for receiving an elongate guide wire, a first end, and an open second end;

a handle on which the tubing is removably fastened in a spiral wrap, the handle being formed in an arc within the curve of the spiral wrap, the handle having a digit-engagement section disposed within the spiral wrap defining a plurality of digit-engaging recesses formed in series for receiving fingers of a user;

a curved outer platform rigidly attached to the handle and located outside the curve of the spiral wrap, the platform being radially aligned with a portion of the digit-engagement section; and a wire dispensing nozzle secured to a forward end of the curved outer platform for closely receiving and tangentially dispensing the guide wire from the apparatus, wherein the elongate tubing is fastened to the handle with the open second end adjacent a rear end of the platform, the guide wire extending across the platform so as to be accessible for manual contact and sliding movement by the thumb of a user.

23. The apparatus of claim 22 wherein one of the digit-engaging recesses comprises a trigger finger recess radially aligned with the wire dispensing nozzle and shaped to receive an index finger of a user, and wherein the other digit-engaging recesses extend in series adjacent said trigger finger recess and are shaped to receive the remaining three fingers.

24. The apparatus of claim 23 wherein trigger finger recess opens in a direction generally tangential to the spiral wrap and the other digit-engaging recesses open radially inward.

25. The apparatus of claim 22 wherein the handle, curved outer platform and dispensing nozzle are molded as a single part.

26. The apparatus of claim 25 wherein the handle includes two clips for receiving and retaining the tubing in the spiral wrap, the handle having a curved outer wall from which the clips extend radially outward, the elongate tubing being held in close proximity and along the curve of the outer wall by the clips.

27. The apparatus of claim 26 wherein the curved outer platform is spaced from the curved outer wall and bridges the two clips.

28. The apparatus of claim 27 wherein the dispensing nozzle is formed as an outward extension of a forward one of the two clips, the second clip being spaced circumferentially therefrom in a rearward direction.

29. The apparatus of claim 28 further including a third clip for receiving and retaining the tubing in the spiral wrap spaced circumferentially rearward from the second clip.

30. The apparatus of claim 29 wherein the third clip has two recesses to receive adjacent loops of the spiral wrap of tubing.

31. The apparatus of claim 22 further including a tapered introducer tip removably received in the dispensing nozzle and extending tangentially with respect to the spiral wrap.

* * * * *